(12) United States Patent
Ding et al.

(10) Patent No.: US 7,234,475 B2
(45) Date of Patent: Jun. 26, 2007

(54) DENTAL FLOSSER

(75) Inventors: Song Jun Ding, Scarborough (CA); Steven A. Slabine, Chestnut Hill, MA (US)

(73) Assignee: Lordan Laboratories, Inc., Newton, MA (US)

( * ) Notice: Subject to any disclaimer, the term of this patent is extended or adjusted under 35 U.S.C. 154(b) by 422 days.

(21) Appl. No.: 10/744,811

(22) Filed: Dec. 23, 2003

(65) Prior Publication Data
US 2004/0134512 A1   Jul. 15, 2004

(30) Foreign Application Priority Data
Dec. 30, 2002  (CN) ................ 02 2 50782

(51) Int. Cl.
*A61C 15/00* (2006.01)
(52) U.S. Cl. .................................... 132/323
(58) Field of Classification Search ............ 132/321, 132/323–329; 206/368–370
See application file for complete search history.

(56) References Cited

U.S. PATENT DOCUMENTS

| | | | |
|---|---|---|---|
| 380,739 A | 4/1888 | Bacon | |
| 691,581 A | 1/1902 | Baumeister | |
| 1,217,264 A | 2/1917 | Baxter | |
| 1,306,998 A * | 6/1919 | Dimitroff | 132/325 |
| 1,364,367 A | 1/1921 | Goodrich | |
| 1,417,518 A * | 5/1922 | Henerlau | 132/324 |
| 1,882,204 A * | 10/1932 | Zrna | 132/323 |
| 2,176,069 A * | 10/1939 | Goulet | 132/327 |
| 2,492,291 A | 12/1949 | Johnson | |
| 2,735,436 A | 2/1956 | Russo | |
| 2,873,749 A | 2/1959 | Gjerde | |
| 3,631,869 A | 1/1972 | Espinosa | 132/91 |
| 4,094,328 A | 6/1978 | Ray | 132/91 |
| 4,206,774 A | 6/1980 | Griparis | |
| 4,253,477 A | 3/1981 | Eichman | |
| 4,657,033 A | 4/1987 | Dalton | 132/91 |
| 4,706,694 A * | 11/1987 | Lambert | 132/323 |
| 4,736,757 A | 4/1988 | Badoux | 132/91 |
| 4,827,952 A * | 5/1989 | Kos | 132/323 |
| 4,920,992 A | 5/1990 | Preciutti | |
| 4,982,752 A * | 1/1991 | Rodriguez | 132/327 |
| 5,010,906 A | 4/1991 | Preciutti | |
| 5,125,424 A | 6/1992 | Eisen | |
| 5,183,064 A | 2/1993 | Barth | |

(Continued)

FOREIGN PATENT DOCUMENTS

JP    1227752    9/1989
WO   WO 0232341   4/2002

*Primary Examiner*—Todd E. Manahan
*Assistant Examiner*—Rachel A. Running
(74) *Attorney, Agent, or Firm*—Mirick O'Connell DeMallie & Lougee LLP

(57) ABSTRACT

A dental flosser is moveable between a stored, non-use position where the flosser is substantially planar, and an engaged or in-use position where a portion of the flosser is angled relative to the handle to aid in reaching back teeth. The dental flosser preferably includes a holder (which may be a U-shaped holder) that is movable between the non-use and in-use position; a handle; a living hinge between the holder and the handle, and a locking arm designed to secure the holder in the in-use position.

14 Claims, 8 Drawing Sheets

U.S. PATENT DOCUMENTS

| | | | |
|---|---|---|---|
| 5,279,315 A * | 1/1994 | Huang | 132/324 |
| 5,375,615 A | 12/1994 | Wahlstrom | |
| 5,483,982 A | 1/1996 | Bennett et al. | |
| 5,538,023 A | 7/1996 | Oczkowski et al. | 132/323 |
| 5,581,838 A * | 12/1996 | Rocco | 15/110 |
| 5,692,531 A | 12/1997 | Chodorow | 132/323 |
| 5,782,250 A | 7/1998 | Harrah, Jr. | |
| D401,701 S | 11/1998 | Chodorow | D28/64 |
| 5,829,458 A | 11/1998 | Chodorow | 132/323 |
| 5,904,153 A | 5/1999 | Meibauer | |
| 5,975,296 A * | 11/1999 | Dolan et al. | 206/368 |
| 6,006,762 A | 12/1999 | Hsia | |
| 6,065,479 A | 5/2000 | Chodorow | 132/323 |
| 6,155,274 A | 12/2000 | Stein | |
| 6,164,294 A | 12/2000 | Takabu | |
| 6,571,804 B2 * | 6/2003 | Adler | 132/325 |
| 6,752,158 B1 | 6/2004 | Gwen | 132/327 |
| 2001/0052349 A1 | 12/2001 | Thaleck | |
| 2002/0106607 A1 | 8/2002 | Horowitz | |
| 2003/0098037 A1 | 5/2003 | Dougan et al. | |
| 2005/0217692 A1 * | 10/2005 | Chodorow et al. | 132/323 |

* cited by examiner

DENTAL FLOSSER

PRIORITY INFORMATION

This application claims priority from Chinese patent application number 02250782.5 which was filed on Dec. 30, 2002 and whose contents are hereby incorporated by reference.

TECHNICAL FIELD

The invention is in the field of dental care products and, more particularly, to an angled dental flosser including a living hinge for moving the flosser between a non-engaged and an engaged position.

BACKGROUND OF RELATED ART

Various dental flossers which hold dental floss are well known in the art. For example, Japanese Patent JP1227752 and World Patent WO 0232341 disclose two such dental floss holders. JP 1227752 discloses a holder including a U-shaped holder having a pair of arms that hold a strand of dental floss in tension there between. The holder further includes a handle, with its distal end extending from the bottom of the U-shaped holder. The handle and U-shaped holder are planar, i.e. flat, so the dental floss holder is portable and easy packed. However, because it is flat, this design can be difficult to use when flossing hard to reach areas, such as when cleaning the back teeth. World Patent WO 0232341 discloses a dental floss holder including a U-shaped holder that also holds a strand of dental floss in tension between the arms, and a planar handle. Disposed between the U-shaped holder and the planar handle is a bowed portion which provides a space for the corners of the user's mouth when the teeth at the back of the mouth are cleaned. Because the dental flosser includes a bow, it is not a planar holder, and its three dimensional design allows it to reach more easily between the back teeth than a flat holder. However, its three dimensional, non planar structure makes it more difficult to stack or display in the package during storage or transit. Other types of dental floss holders are also well known in the art.

There is therefore a continued need in the art for a disposable dental flosser which effectively flosses between teeth, including back teeth or other hard to reach areas in the mouth, and which is portable and can be readily stored, displayed and packed.

SUMMARY

An object of the present invention is to provide a dental flosser, including a holder and a length of dental floss, which effectively flosses between teeth, including back teeth, and which is easy to store and transport.

In accordance with one aspect, there is provided a dental flosser which is moveable between a stored, non-use position where the flosser is substantially planar, and an engaged or in-use position where a portion of the flosser is angled relative to the handle. The dental flosser preferably includes a holder (which may be a U-shaped holder) that is movable between the non-use and in-use position; a handle; a living hinge between the holder and the handle, and a locking arm designed to secure the holder in the in-use position. In one embodiment, the locking arm is disposed between the arms of the U-shaped holder and is engageable with the distal end of the handle in the in-use position. In this embodiment, the locking arm may preferably be supported at the bottom of the U-shaped holder, includes a locking head, and is bendable in order to engage the handle. In the in-use or locked position, the head of the locking arm is secured to by a corresponding locking member supported on the handle. The head can be released from the locking member by the user, as desired. This allows the user to selectively engage and release the locking arm from the handle, as desired. In another embodiment, the locking arm is supported on the handle and is engageable with an aperture disposed at the bottom of the U-shaped holder in order to lock the U-shaped holder into the in-use position. In another embodiment, the U-shaped holder includes more than one aperture to receive the locking arm so that the U-shaped holder can be selectively angled.

The embodiments may preferably include a living hinge disposed between the handle and the U-shaped holder. The living hinge is bendable and designed so that the U-shaped holder will bend transversely at an appropriate degree for reaching between teeth. The flosser also preferably includes a strand of floss in tension which spans the arms of the U-shaped holder. The U-shaped holder, handle and the locking arm are substantially planar, i.e. flat, in the non-use position and thus easy packed and portable. By bending the living hinge and locking it with the locking member, a triangular structure for cleaning teeth, and which can readily reach the back teeth of the mouth, is formed.

BRIEF DESCRIPTION OF THE DRAWINGS

It should be understood that the drawings are provided for the purpose of illustration only and are not intended to define the limits of the invention. The foregoing and other objects and advantages of the embodiments described herein will become apparent with reference to the following detailed description when taken in conjunction with the accompanying drawings in which.

DETAILED DESCRIPTION OF THE ILLUSTRATIVE EMBODIMENTS

Figure 1:
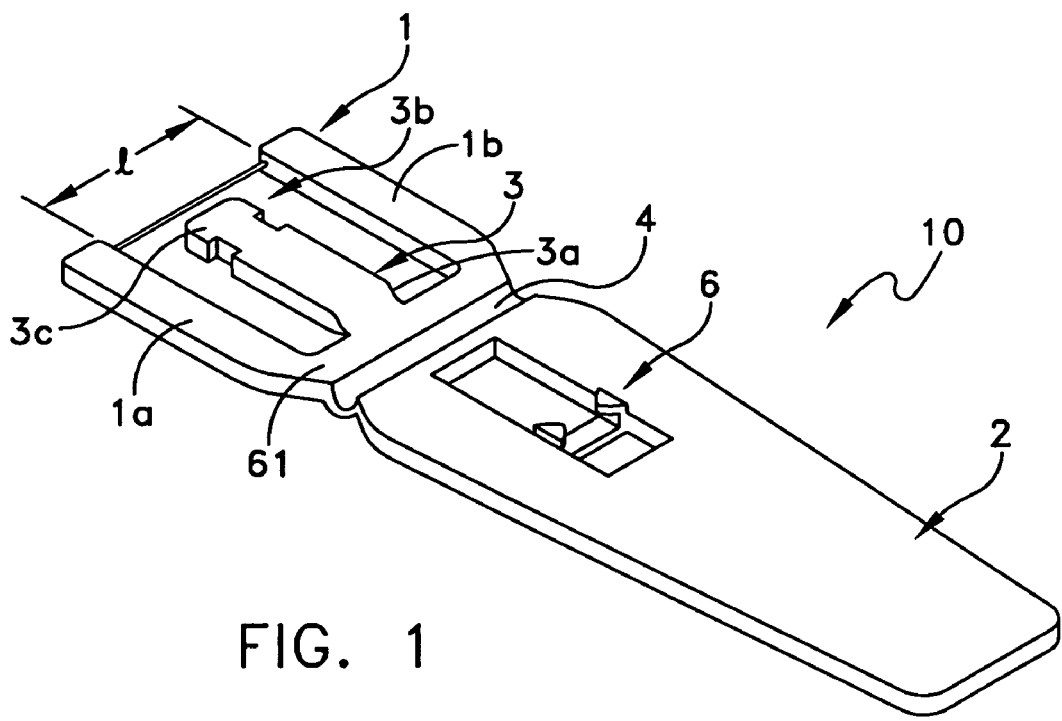
FIG. 1 is a perspective view of a first embodiment of the dental flosser in the non-use position.

A dental flosser 10 for cleaning teeth is illustrated in FIGS. 1–14. A first embodiment, illustrated in FIGS. 1–2 preferably includes a floss holder 1 movable between an initial, non-use position (FIG. 1) and an engaged or in-use position (FIG. 2), a handle 2 and a locking arm 3 designed to secure the holder in the engaged position. In the present embodiment, the holder is preferably a U-shaped holder supported at a distal end of the handle 2 by a bendable, living hinge 4. As used herein, the term "living hinge" or "integral hinge" is used as is conventional to mean a section of plastic that connects two pieces and which allows the pieces to be moved relative to each other. The hinge 4 preferably extends from the distal end of the handle and connects with the bottom of the U-shaped holder 1 so that the U-shaped holder can bend transversely at an appropriate degree during use. The base, or bottom 61 of the U-shaped holder should have a thickness sufficient to avoid deformation of the U-shaped holder during use. In the present embodiment, locking arm 3 is supported at a first end 3a on the bottom of the U-shaped holder, between the arms of the member. The locking arm 3 is bendable at its first end 3a so that it can converge toward the handle and be secured thereto during use. The second end 3b of the locking arm 3 is designed to be secured to the handle 2.

The second end 3b of the locking arm may preferably include a locking head 3c which is engageable with a corresponding locking member 6 supported on handle 2. The locking head 3c may include a pair of cut-outs which engage projections of the locking member 6 in order to secure the U-shaped holder in an upright, or engaged position during use. In the present embodiment, the U-shaped holder is supported at approximately a 90 degree angle relative to the handle during use, but other angles may be utilized as would be known to those of skill in the art. To move the U-shaped holder back into the planar or flat initial position, the locking arm is released from engagement with the handle. In the non-engaged position the U-shaped holder 1, the handle 2 and the locking arm 3 are all flat or planar, i.e., the angle between the U-shaped holder and handle is about 180, degrees making the device easy to carry and pack without the associated risk of damage that would be inherent if the device were packed with the U-shaped holder raised and apt to bend.

Figure 2:
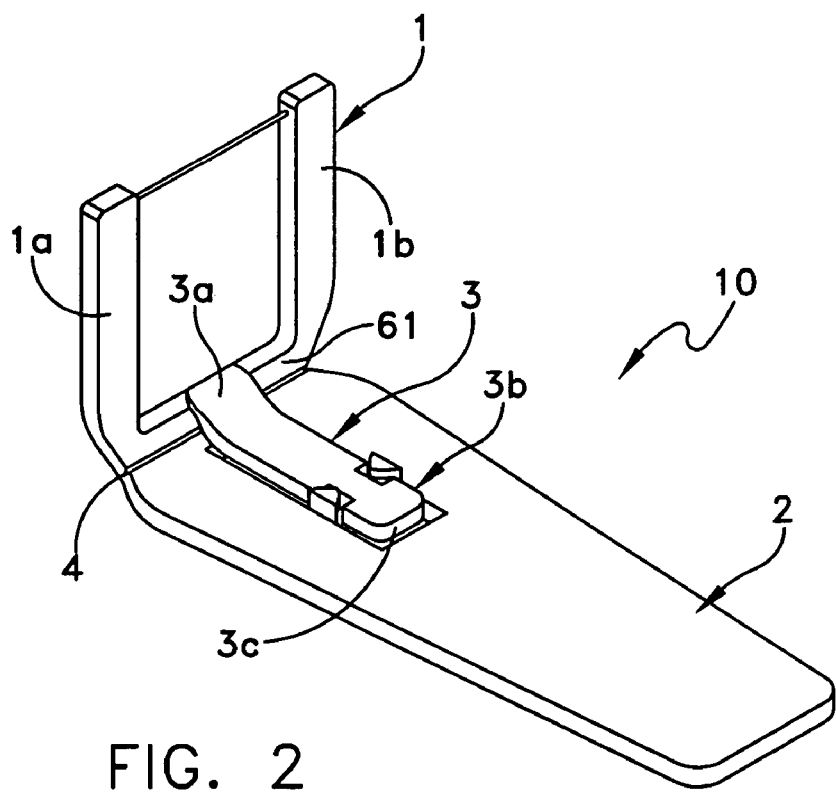
FIG. 2 is a perspective view of the flosser of FIG. 1 in the in-use position.

FIG. 2 illustrates the dental flosser in the engaged, or in-use position. As described above, in this position the U-shaped holder 1 is bent at the hinge 4, while the locking arm 3 is bent at the first end toward the handle 2 and is secured thereto. A firm triangle structure is thus formed by the U-shaped holder 1, handle 2 and locking arm 3. The U-shaped holder 1 supports a length of floss "1" in tension between its arms 1a, 1b, and bends at an appropriate angle toward handle 2 so that the back teeth are easy to reach with the floss, thus making them convenient to clean.

Figure 3:
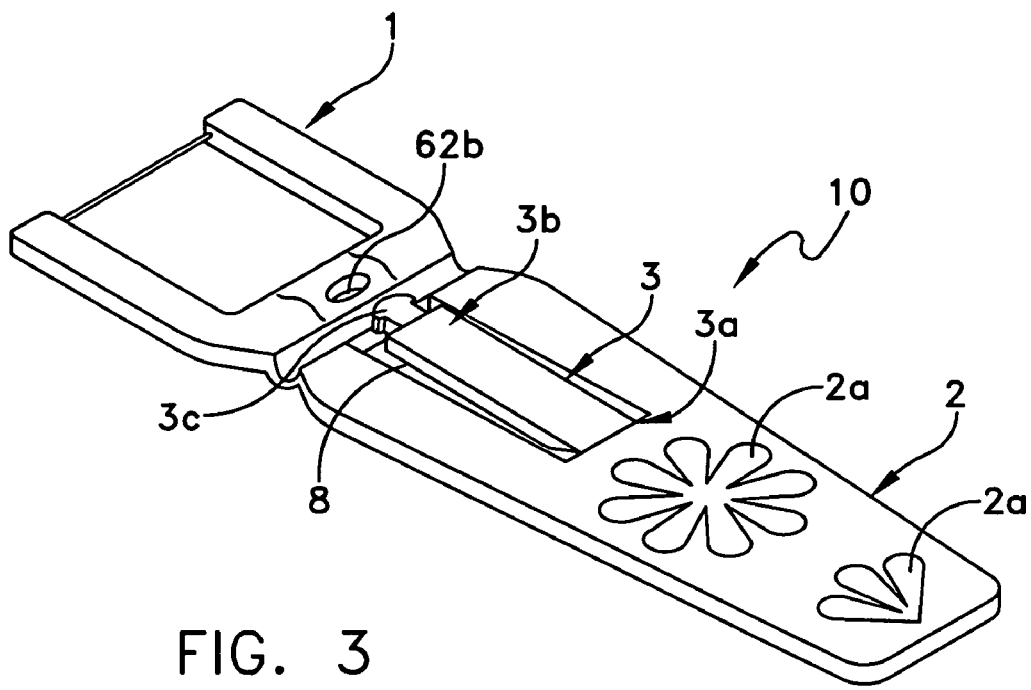
FIG. 3 is a perspective view of a second embodiment of the dental flosser in the non-use position.

Referring now to FIG. 3, a second embodiment of a dental flosser is shown, before use. As with the first embodiment, the second embodiment includes a U-shaped holder 1 supported at a distal end of handle 2 by a living hinge 4, and a locking arm 3 for securing the U-shaped holder in an angled, or engaged position during use. The hinge 4 preferably extends from the distal end of the handle and connects with the bottom of the U-shaped holder 1 so that the U-shaped holder can bend transversely at an appropriate degree during use, as discussed above. One difference between the first embodiment and the second embodiment is that in the second embodiment, the locking arm 3 is supported on the handle 2 instead of on the U-shaped holder. The U-shaped holder further includes an aperture 62b for receiving and locking the second end 3b of the locking arm therein. In the second embodiment, the locking arm is fixed at its first end 3a to the handle, and is bendable at the first end such that the locking head 3c can be inserted into the aperture 62b in order to secure the U-shaped holder in the engaged or in-use position. The aperture 62b is preferably disposed along a bottom of the U-shaped holder, as shown.

Figure 4:
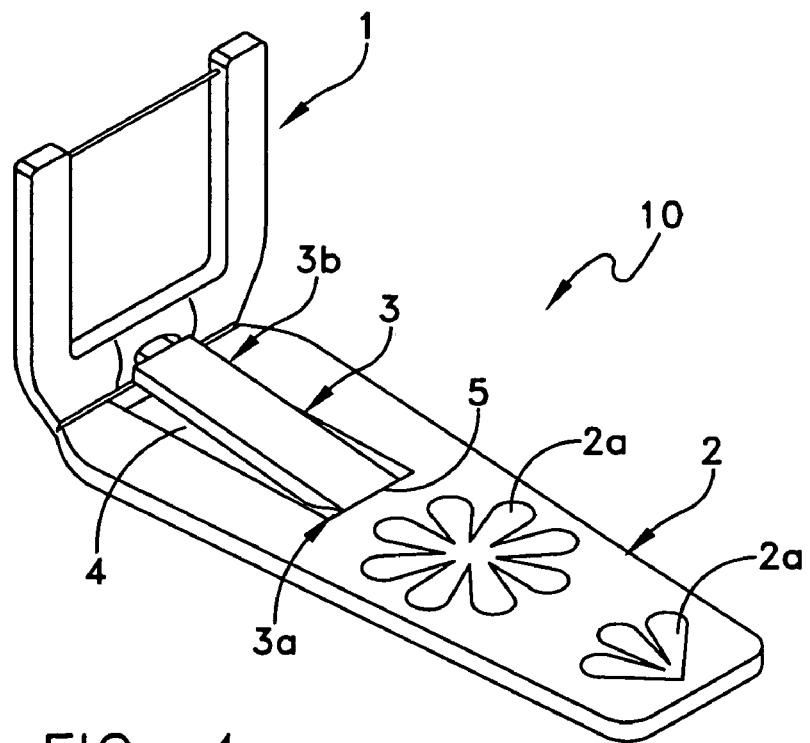
FIG. 4 is a perspective view of the flosser of FIG. 3 in the in-use position.

FIG. 4 illustrates the second embodiment during use, i.e. in the engaged position. In use, the U-shaped holder 1 bends at the living hinge 4 while the locking arm 3 bends at a bendable hinge 5 adjoining the first end of the locking member and the handle 2. The second end of the locking arm 3 supports locking head 3c which engages the aperture 62b disposed in the bottom of U-shaped holder 1 to lock the U-shaped holder in place. A secure triangle structure is thus formed by U-shaped holder 1, handle 2 and locking arm 3. The U-shaped holder 1 bends at an appropriate angle toward the handle 2 for convenience of cleaning the back teeth, as discussed above.

In the present embodiment, a clearance space 8 may be disposed between the locking arm and the handle to facilitate bending the locking arm. The flosser may optionally include a concave-convex design 2a on handle 2 which is decorative and also serves as an anti-slide function to facilitate gripping the handle.

The length of the locking arm 3 may be varied, as would be known to those of skill in the art. At certain lengths, the locking arm 3 may partially interfere with the bottom body of the U-shaped holder 1 thus making it difficult to stack the flossers. Reducing the thickness of the interfering part of the locking arm 3 and the U-shaped holder 1 resolves the issue. Alternatively, forming an aperture at the interfering part of the bottom of the U-shaped holder 1 also resolves the issue as shown in FIGS. 5 and 6.

Figure 5:
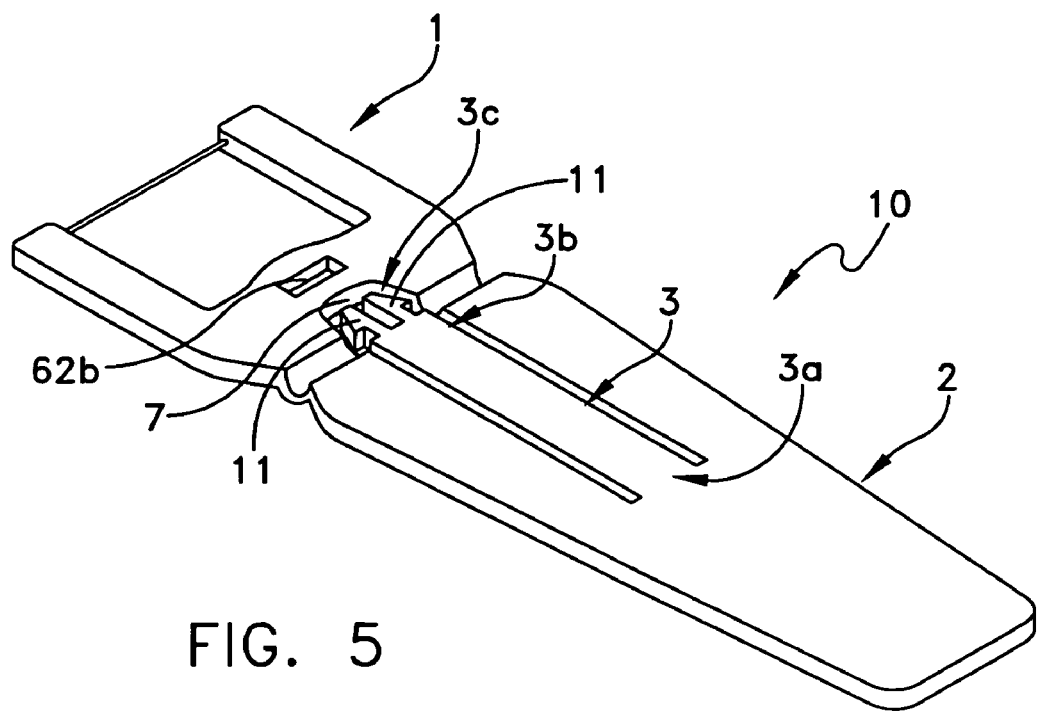
FIG. 5 is a perspective view of a third embodiment of the dental flosser in the non-use position.
Figure 6:
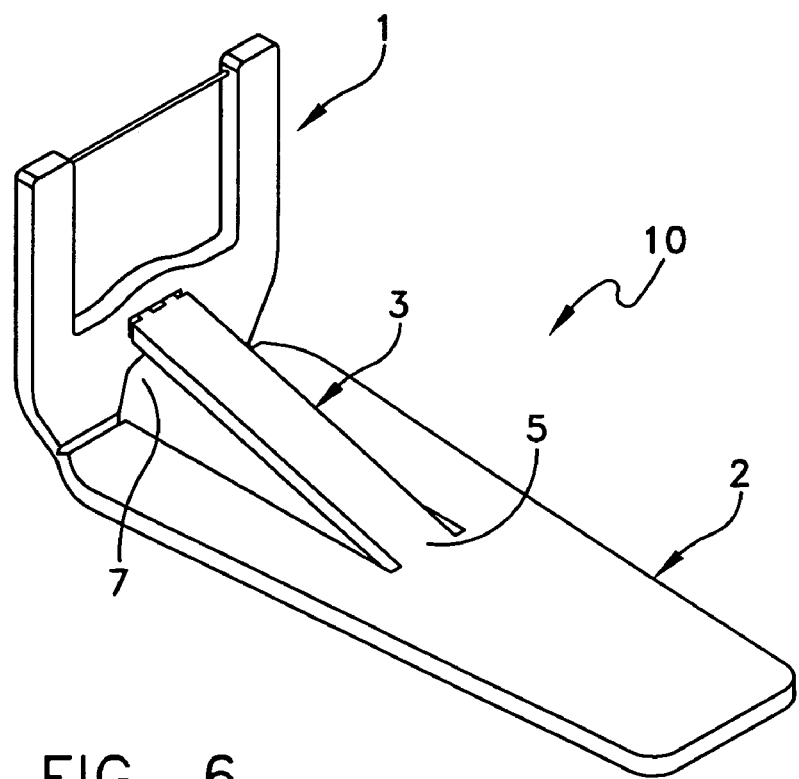
FIG. 6 is a perspective view of the flosser of FIG. 5 in the in-use position.

Referring now to FIGS. 5 and 6, a third embodiment is shown before use and in use, respectively. In this embodiment, the locking arm 3 is likewise supported on the handle 2 for engaging an aperture 62b disposed in the base of the U-shaped holder. However, the length of the locking arm is such that the second end 3b of the locking arm extends into an opening 7 formed in the bottom of the U-shaped holder in the non-engaged, non-use position. In this embodiment, locking head 3c includes a pair of arms 11 which are able to flex toward and away from each other in order to allow the arm to be inserted and released from within the first aperture 62b, as discussed in greater detail below with respect to the fifth embodiment.

In other respects, the third embodiment is similar to the second embodiment. In use, the U-shaped holder 1 bends at the living hinge 4 while the locking arm 3 bends at a bendable hinge 5 adjoining the first end of the locking member and the handle. The second end of the locking arm 3 engages the aperture 62b in the bottom of U-shaped holder 1 to secure it. A secure triangle structure is thus formed by U-shaped holder 1, handle 2 and locking arm 3. The U-shaped holder 1 bends at an appropriate angle toward the handle 2 for convenience of cleaning the back teeth, as discussed above. When in the non-use position, the head 3c of the locking arm 3 rests in the opening 7.

Figure 7:
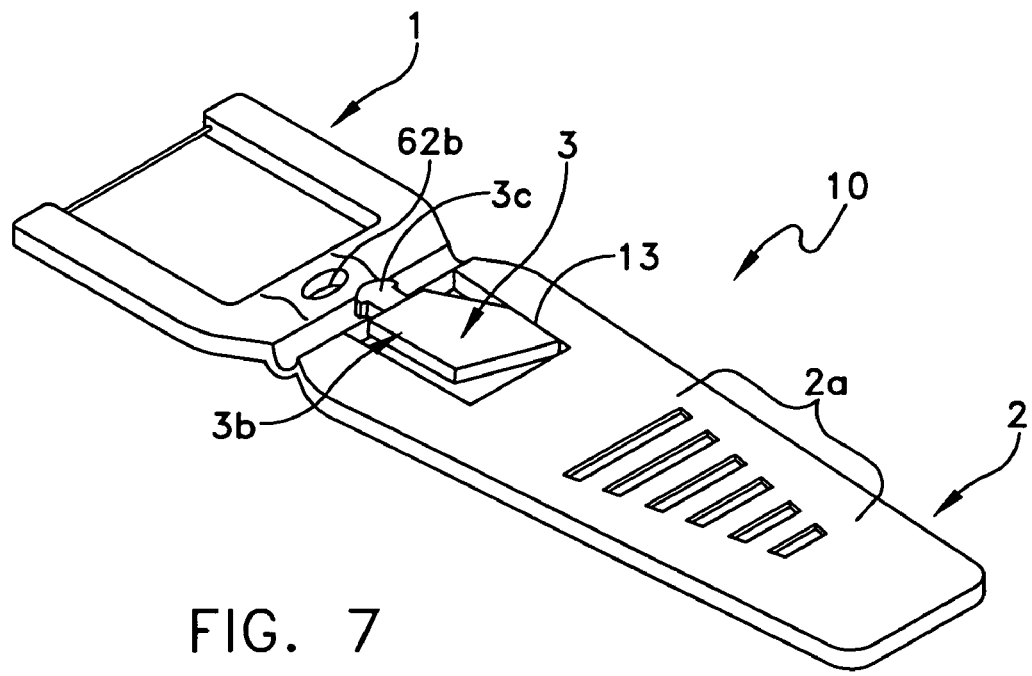
FIG. 7 is a perspective view of a fourth embodiment of the dental flosser in the non-use position.
Figure 8:
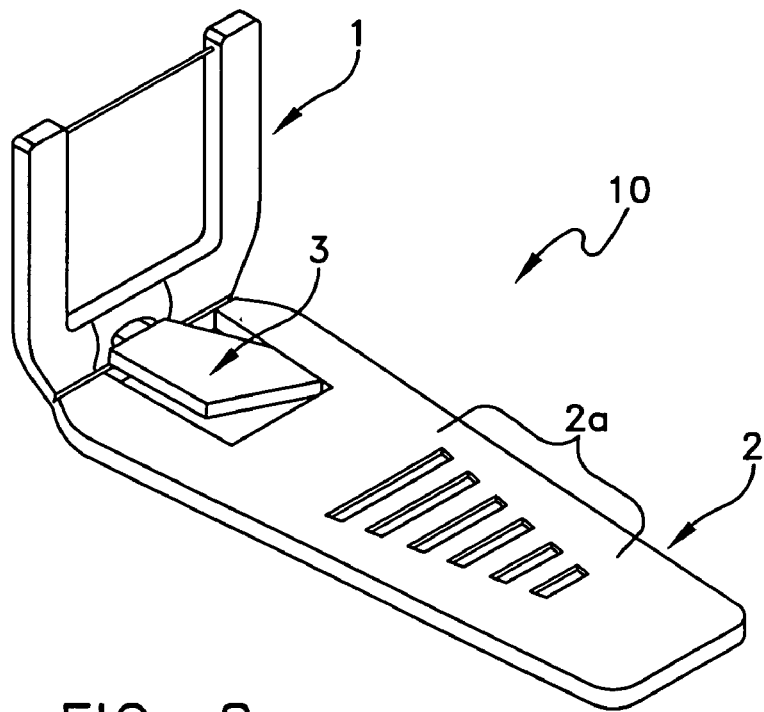
FIG. 8 is a perspective view of the flosser of FIG. 7 in the in-use position.
Figure 9:
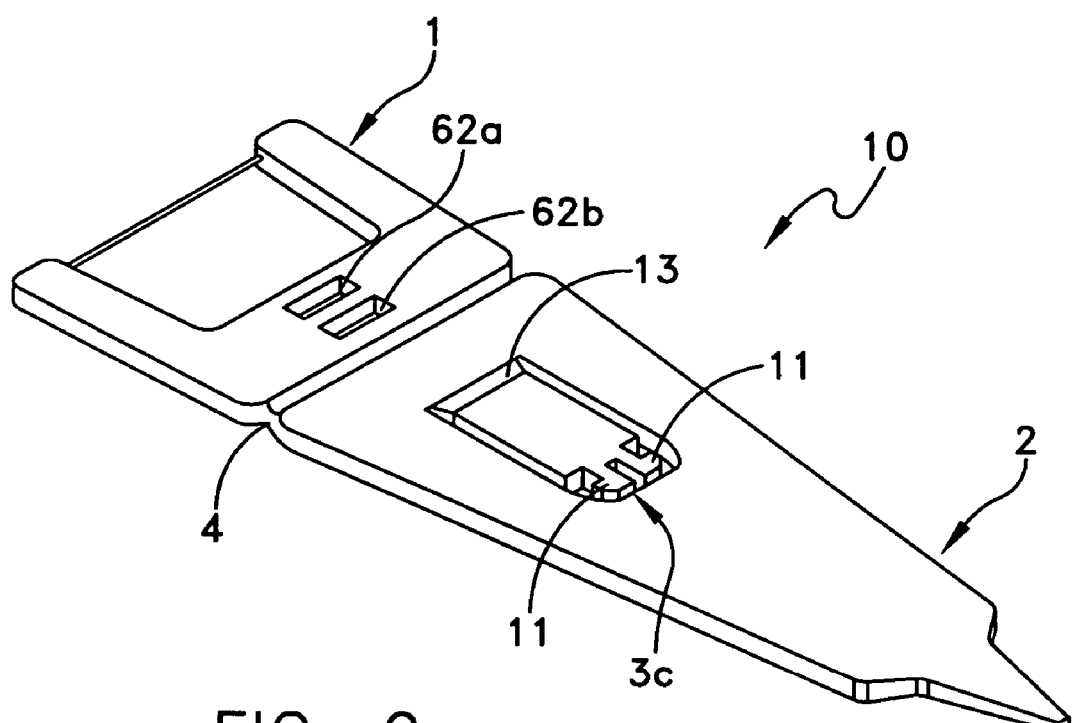
FIG. 9 is a perspective view of a fifth embodiment of the dental flosser in the non-use position.

Referring now to FIGS. 7 and 8, a fourth embodiment is shown before use and in use, respectively. In this embodiment, the locking arm 3 is joined to the handle 2 along a side edge 13 and is angled upward so that locking head 3c can releasably engage aperture 62b as discussed above with respect to the second embodiment. The present embodiment may also include an anti-slide stripe 2a on handle 2 to facilitate gripping the handle. In all other respects, the fourth embodiment is similar to the second embodiment discussed above.

Figure 10:
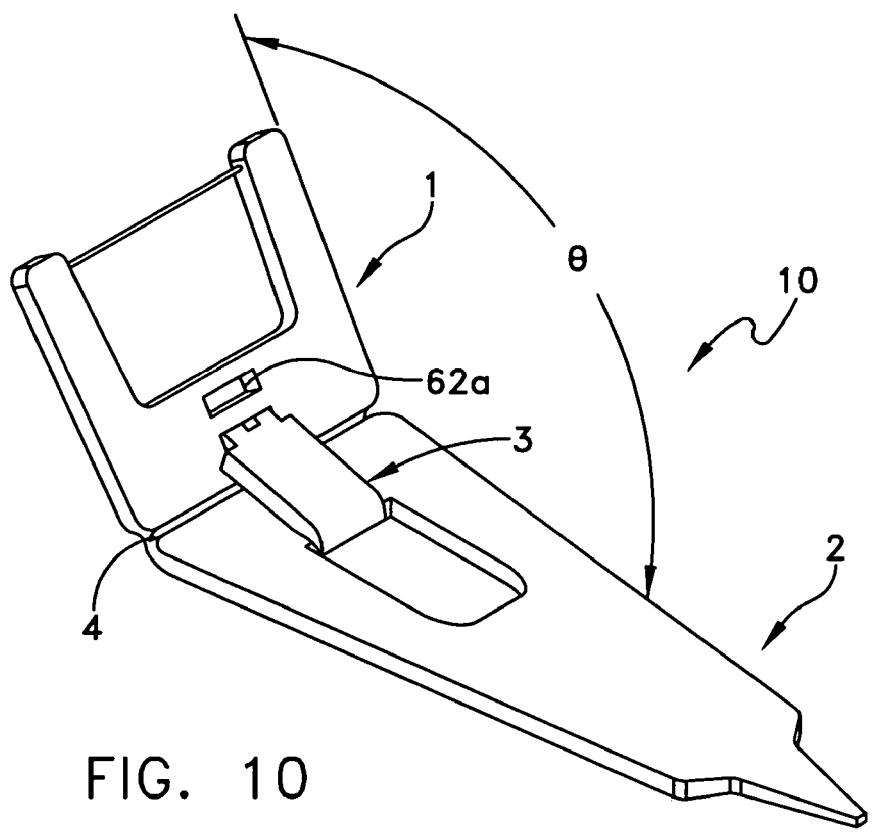
FIG. 10 is a perspective view of the flosser of FIG. 9 at a first angle in the in-use position.
Figure 11:
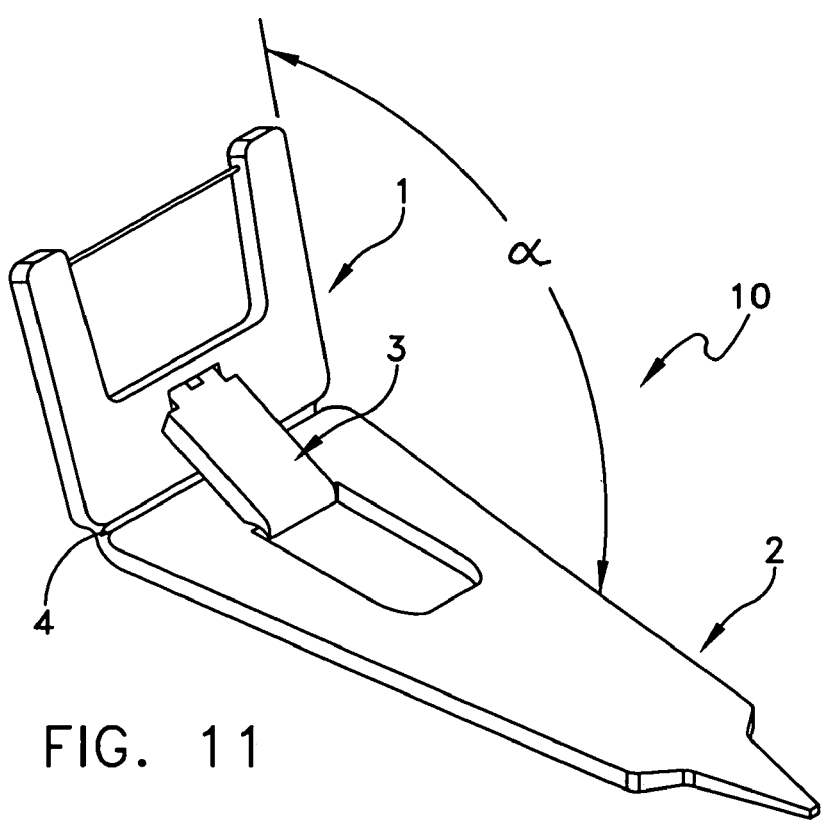
FIG. 11 is a perspective view of the flosser of FIG. 9 at a second angle in the in-use position.
Figure 12:
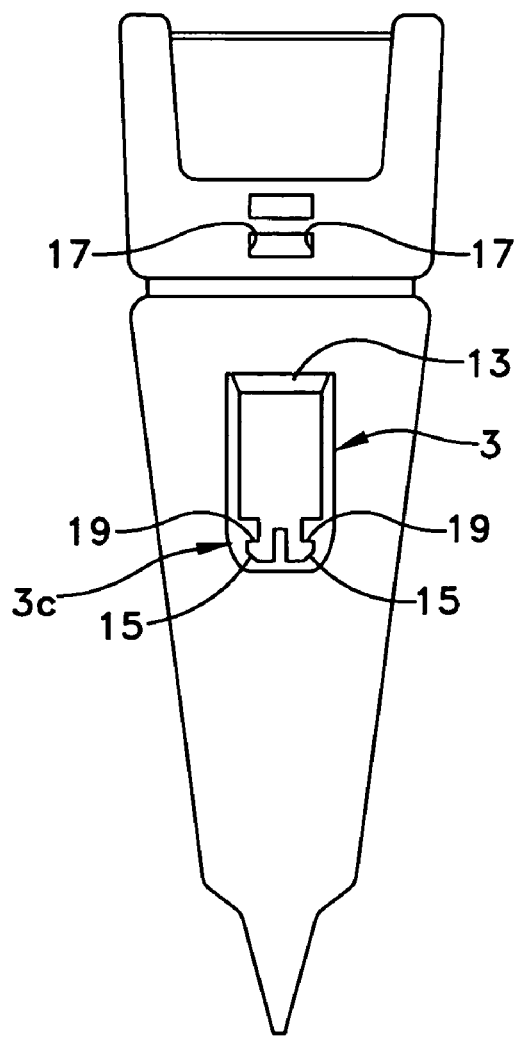
FIG. 12 is a top plan view of the flosser of FIG. 9.
Figure 13:
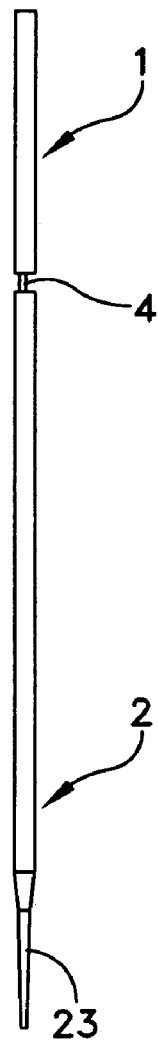
FIG. 13 is a side view of the flosser of FIG. 9.
Figure 14:
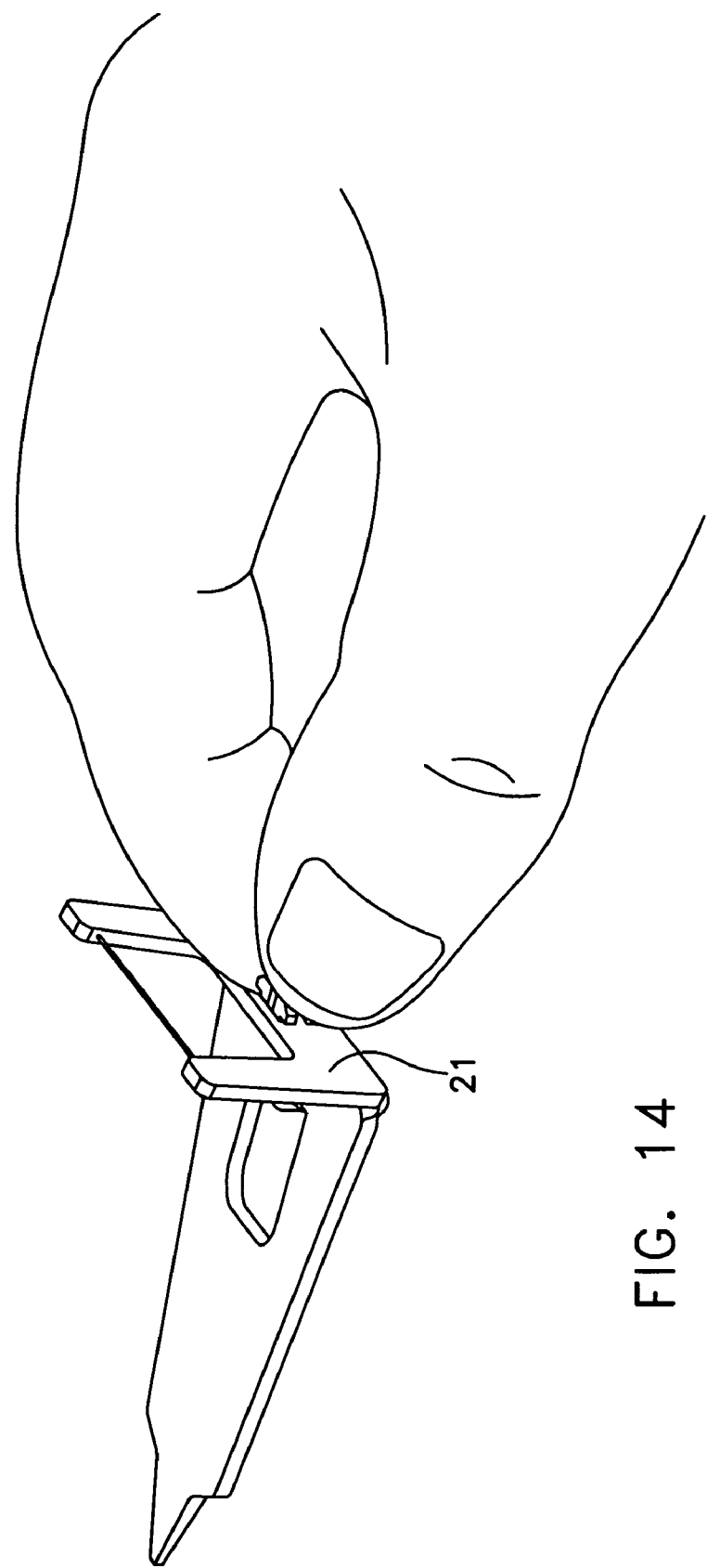
FIG. 14 is a rear, perspective of the flosser of FIG. 9 being disengaged from use.

FIGS. 9–14 illustrate a fifth embodiment of a dental flosser 10. In this embodiment, the U-shaped holder is adjustable between at least two positions in order to vary the angle of the U-shaped holder 1 relative to the handle 2. As illustrated, the fifth embodiment includes U-shaped holder 1 supported at a distal end of handle 2 by a living hinge 4, a locking arm 3 for securing the U-shaped holder in an upright, or engaged position during use, a handle for holding the flosser, and a pair of apertures 62a, 62b for selectively supporting the U-shaped holder at a pre-determined angle relative to the handle 2. Apertures 62a, 62b are preferably disposed on the bottom of U-shaped holder 1 and are longitudinally spaced from each other. In this manner, if the lower aperture 62b is engaged by the locking arm 3, the U-shaped holder is supported at an angle θ relative to the handle 2 (FIG. 10). However, if the upper aperture 62a is engaged by locking arm 3, then the U-shaped holder is supported at an angle α relative to the handle 2 (FIG. 11). In the present embodiment, angle θ is preferably greater than about 90 degrees, while angle α is about 90 degrees, although other angles may be utilized as would be known to those of skill in the art. In order to further vary the angle between the U-shaped holder and the handle, additional apertures may be utilized, and/or the length of the locking arm may be varied for different flossers.

The locking arm in the fifth embodiment may be secured to the handle at a distal end by a hinge 13, instead of at a proximal end as illustrated in embodiments two and three. The head 3c of the locking arm may include a pair of arms 11 which are able to flex toward and away from each other in order to allow the arm to be inserted and released from within the first and second apertures 62a, 62b, respectively. As the head 3c of the locking arm is inserted into either aperture 62a, 62b the sides 15 of the head (which may be ramped), contact the side walls 17 of the aperture thus creating pressure on the arms so that the arms flex inward, toward each other, allowing the head 3c to enter the aperture. Once inserted, the pressure is released and the arms 11 flex outward, away from each other, and the locking arm is secured by the bottom 19 of the locking head 3c engaging the back surface 21 of the U-shaped holder. In order to disengage the locking arm from the U-shaped holder, the arms 11 are forced together by a user (FIG. 14), thus allowing the head 3c to pass back through the aperture, toward the handle 2, to release the U-shaped holder. The present embodiment may further include a pointed section 23 on the proximal end of the handle which can be used as a tooth pick, if desired. This embodiment also includes a length of floss held in tension, and a clearance between the locking member and the handle, as discussed above.

It will be understood that various modifications may be made to the embodiment disclosed herein. Therefore, the above description should not be construed as limiting, but merely as exemplifications of a preferred embodiment. For example, the shape of the U-shaped holder may be varied, as may the shape of the handle and locking member. Those skilled in the art will envision other modifications within the scope spirit of the invention.

What is claimed is:

1. A dental flosser for supporting a length of floss comprising:
   a handle including a distal end and a proximal end, the handle being constructed and arranged to be grasped by a user;
   a floss holder supported on the distal end of the handle by a living hinge and movable between a first position and a second position;
   at least one aperture supported on one of the movable floss holder and the handle;
   a locking arm pivotally supported opposite the aperture on the other of the movable holder and the handle so as to be movable between at least a first and a second position and including a locking head constructed and arranged to releasably engage the aperture; and
   wherein the floss holder is pivotal and the locking movable between at least a first unlocked position and a second, engaged position where the locking head engages the locking aperture so as to secure the movable holder in a second position relative to the handle.

2. The dental flosser of claim 1, wherein the floss holder has a generally U-shaped configuration including a bottom, and a pair of arms constructed and arranged to support a length of floss there between.

3. The dental flosser of claim 1, wherein the at least one aperture includes a first aperture and a second aperture spaced from each other in the bottom of the holder, and wherein engagement of the locking head in the first aperture supports the holder at a first angle relative to the handle and engagement of the locking head in the second aperture supports the holder at a second angle relative to the handle, the first and second angles each being less than about 180 degrees.

4. The dental flosser of claim 3, wherein the first angle is greater than about 90 degrees and the second angle is about equal to or less than 90 degrees.

5. The dental flosser of claim 1, wherein the handle includes a textured surface to aid in gripping the handle.

6. The dental flosser of claim 1, wherein the proximal end of the handle includes a pointed section constructed and arranged to reach between teeth.

7. A dental flosser comprising:
   a handle including a distal end and a proximal end, the handle being constructed and arranged to be grasped by a user;
   a movable floss holder including:
   a) a base;
   b) a pair of arms supported by the base; and
   c) a length of floss disposed between the pair of arms;
   at least one locking aperture supported on one of the movable head and the handle;
   a locking arm supported opposite the locking aperture on the other of the movable holder and the handle, the locking arm including a locking head constructed and arranged to fit within the locking aperture; and
   a living hinge disposed between the base of the movable holder and the distal portion of the handle; and
   wherein the holder is movable between a first position where the locking arm and the aperture are spaced from each other to a second position where the locking arm engages the locking aperture so as to secure the holder in a second position relative to the handle.

8. The dental flosser of claim 7, wherein the locking arm is pivotally supported by and extends from the base of the floss holder, and wherein the aperture is disposed within the handle.

9. The dental flosser of claim 8, wherein the locking head includes a pair of cut-out portions for engaging a pair of corresponding projections supported within the aperture.

10. The dental flosser of claim 7, wherein the locking arm is supported on and extends from the handle, and wherein the aperture is disposed within the base of the floss holder.

11. The dental flosser of claim 10, wherein the at least one aperture includes a first aperture and a Second aperture spaced from each other in the bottom of the holder, and wherein engagement of the locking head in the first aperture supports the holder at a first angle relative to the handle and engagement of the locking head in the second aperture supports the holder at a second angle relative to the handle, the first and second angles each being less than about 180 degrees.

12. The dental flosser of claim 11, wherein the first angle is greater than about 90 degrees and the second angle is about equal to or less than 90 degrees.

13. The dental flosser of claim 7, wherein the handle includes a textured surface to aid in gripping the handle.

14. The dental flosser of claim 7, wherein the proximal end of the handle includes a pointed section.

* * * * *